(12) United States Patent
Chiodo

(10) Patent No.: US 6,451,262 B1
(45) Date of Patent: Sep. 17, 2002

(54) DISSECTION SPECIMEN HOLDER

(76) Inventor: Chris D. Chiodo, 29277 Newport, Warren, MI (US) 48093

( * ) Notice: Subject to any disclaimer, the term of this patent is extended or adjusted under 35 U.S.C. 154(b) by 101 days.

(21) Appl. No.: 09/596,500

(22) Filed: Jun. 19, 2000

(51) Int. Cl.[7] .............................. B01L 3/00; G01N 1/06
(52) U.S. Cl. .............................. 422/99; 83/168; 83/407; 83/651.1; 83/932; 422/104
(58) Field of Search ................... 359/356, 398; 434/296, 292; 374/12; D24/224; 422/99, 102, 104; 83/407, 932, 651.1, 168

(56) References Cited

U.S. PATENT DOCUMENTS

| | | | | | |
|---|---|---|---|---|---|
| 4,964,323 | A | * | 10/1990 | Fortney | 83/167 |
| 5,499,578 | A | * | 3/1996 | Payne | 30/114 |
| D372,846 | S | * | 8/1996 | Fortney | D7/673 |
| 5,653,154 | A | * | 8/1997 | Liu et al. | 83/468.5 |
| 5,692,424 | A | * | 12/1997 | Wallace | 83/167 |
| 5,823,079 | A | * | 10/1998 | Liu et al. | 83/13 |
| 5,946,998 | A | * | 9/1999 | Thompson | 269/270 |

* cited by examiner

Primary Examiner—Jill Warden
Assistant Examiner—Elizabeth Quan
(74) Attorney, Agent, or Firm—Lawrence I. Shurupoff

(57) ABSTRACT

A hollow dissection specimen holder has an internal chamber in open and direct communication with a series of dissection guide slots. The roof of the chamber is located above the floor of the slots to allow a razor to pass completely through the specimen and into the top of the chamber to deposit cut tissue and other debris into the chamber.

7 Claims, 3 Drawing Sheets

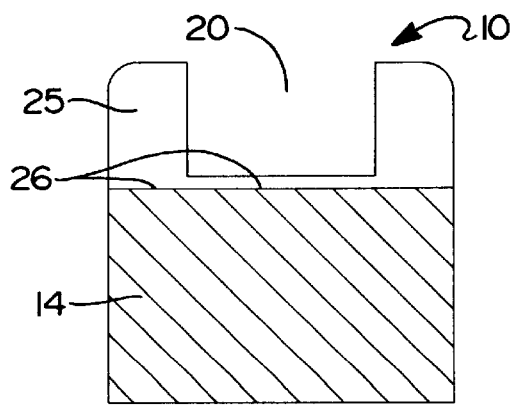
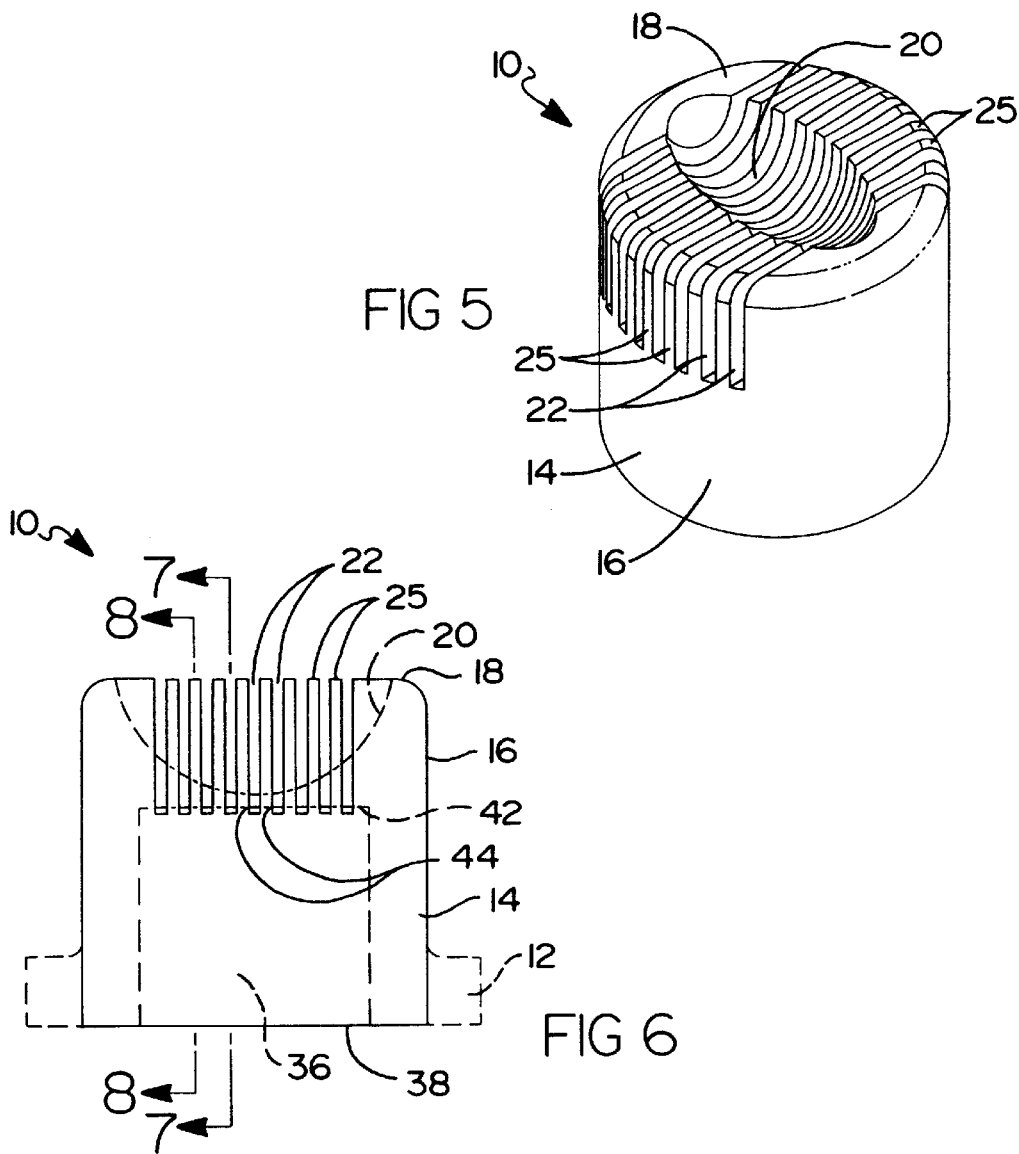

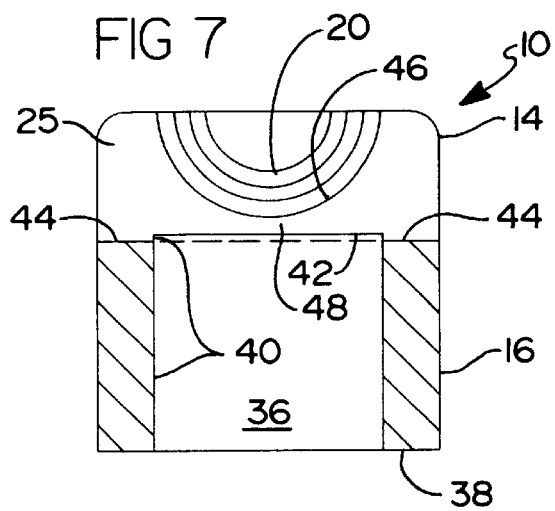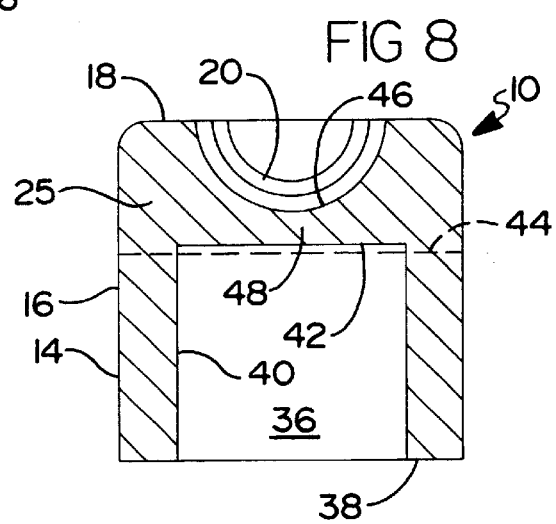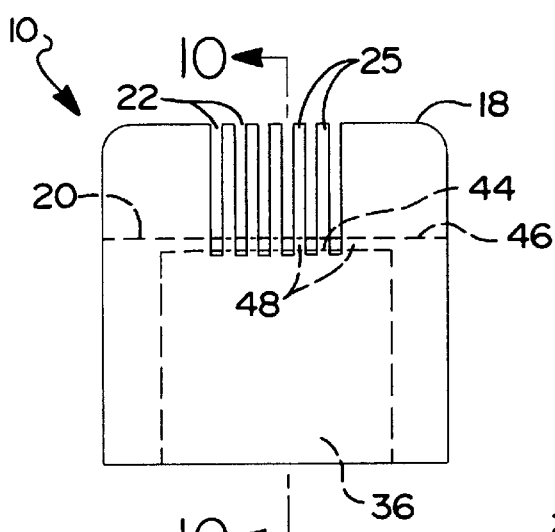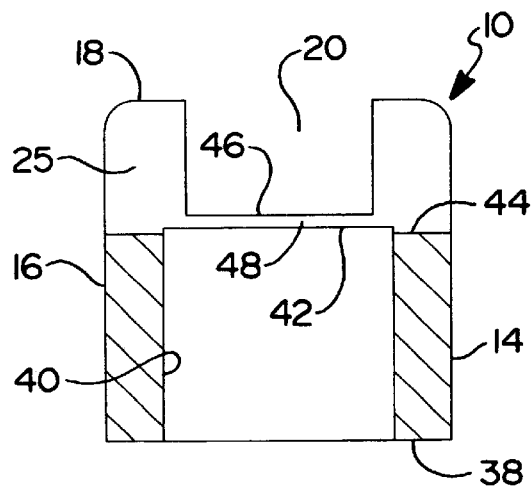

DISSECTION SPECIMEN HOLDER

BACKGROUND OF THE INVENTION

1. Field of the Invention

The present invention relates in general to apparatus for supporting biological specimens during dissection and relates in particular to such apparatus having a series of slicing guide slots communicating with an open cavity for facilitating cleaning and preventing obstruction of the guide slots with tissue and other specimen debris.

2. Description of Prior Developments

Dissection specimen holders have long been used to secure a specimen, such as a rodent brain, as the specimen is sliced in a series of thin parallel sections. A shaped cavity is defined in the upper surfaces of a series of spaced apart parallel support members for receiving and supporting a specimen. A series of parallel guide slots is defined between the plate-like support members. A thin safety razor or similar dissection blade is typically inserted into one of the slots and then into a specimen held in the shaped cavity, which is typically a recess contoured to closely match the shape of the specimen.

As the blade cuts through the specimen, it is guided within one of the guide slots which extends beneath the specimen. Once the blade passes through the specimen, it typically abuts against the floor of the slot. Tissue and other debris adhering to the blade is typically deposited on and around the floor of the slot.

Over time, the debris accumulates to the point where it interferes with the blade before the blade makes a complete cut through the specimen. At this point the debris must be cleaned from the slot or slots before a proper sample cut can be completed. Because the specimen tissue builds up over time, it hardens and strongly adheres to the bottom of the slots. This creates a difficult cleaning problem which often necessitates the prolonged use of ultrasonic cleaning apparatus as well as supplemental cleaning with brushes and the like.

Accordingly, a need exists for a dissection specimen holder which resists the build-up of specimen tissue and other specimen debris.

A further need exists for such an apparatus which facilitates cleaning, particularly around and within the bottom of the guide slots.

SUMMARY OF THE INVENTION

The present invention has been developed to fulfill the needs noted above and therefore has as an object the provision of a dissection specimen holder which resists the accumulation of specimen tissue within a series of guide slots.

A further object of the invention is the provision of a dissection specimen holder which is easy to clean, particularly around and within the lower portions of a series of guide slots which underlie the specimen.

These and other objects are met by the present invention which is directed to a dissection specimen holder having a contoured specimen pocket or cavity formed in the upper surfaces of a plurality of planar vertical support plates. The plates are spaced apart by a series of parallel slots which serve to guide a cutting blade through the specimen.

A significant feature of the invention is the provision of a chamber or opening at the bottom of each guide slot for receiving any debris carried by a cutting blade into the bottom of the guide slot. The chamber or opening communicates with the bottom of each guide slot such that each slot has an open bottom through which any debris may freely pass. By eliminating the floor of each slot, tissue is prevented from accumulating and becoming compacted in the bottom of each slot.

By opening up the bottom of each slot into a relatively large opening, cavity, chamber or the like, cleaning of the guide slots is greatly facilitated. Water or other cleaning fluids may be freely flushed completely through the slots from top to bottom and/or from bottom to top. This allows for a thorough cleaning of the slots while also preventing build up of tissue and other debris.

The aforementioned objects, features and advantages of the invention will, in part, be pointed out with particularity, and will, in part, become obvious from the following more detailed description of the invention, taken in conjunction with the accompanying drawings, which form an integral part thereof.

BRIEF DESCRIPTION OF THE DRAWINGS

In the drawings:

FIG. 4 is a view in section taken through a guide slot of FIG. 3 along section line 4—4 thereof;

FIG. 5 is a perspective view of a dissection specimen holder constructed in accordance with the invention;

FIG. 6 is a side view of the holder of FIG. 5;

FIG. 7 is a view in section taken through a guide slot of FIG. 6 along section line 7—7 thereof;

FIG. 8 is a view in section taken through a support plate of FIG. 6 along section line 8—8 thereof;

FIG. 9 is a side view of a second embodiment of the invention; and

FIG. 10 is a view in section taken through a guide slot of FIG. 9 along section line 10—10 thereof In the various views of the drawings, like reference characters designate like or similar parts.

DETAILED DESCRIPTION OF THE PREFERRED EMBODIMENTS

Figure 1:
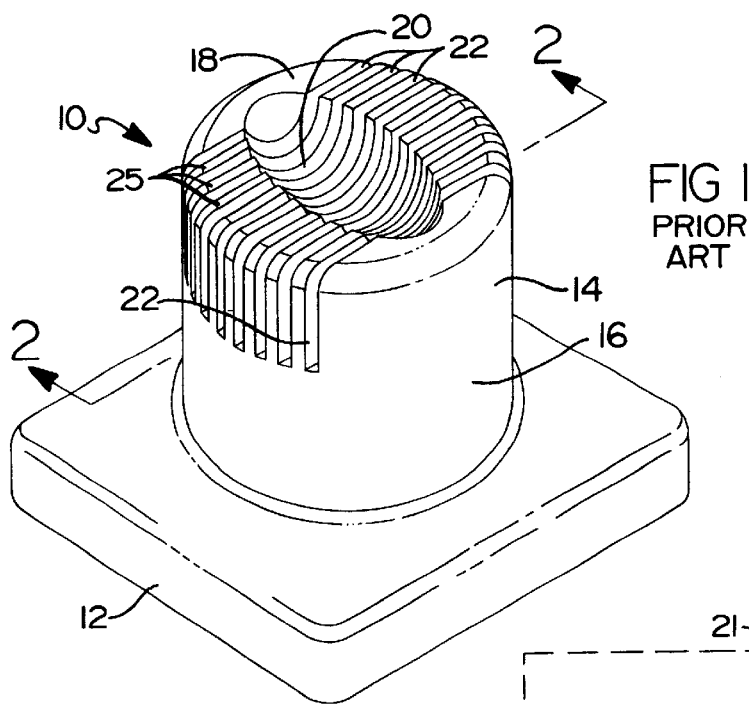
FIG. 1 is a perspective view of a dissection specimen holder constructed in accordance with the prior art.

In order to better appreciate the advantages of the present invention, a brief review of the prior art will be helpful. As seen in FIG. 1, a conventional dissection specimen holder 10 is shown constructed in accordance with a well known design. The holder may be rough cast and then machined or completely machined from stock material. Although many metal materials such as stainless steel may be used to form holder 10, zinc is preferred for its machinability. A subsequent protective plating of chrome or the like is typically applied once the holder is machined and deburred.

A rectangular base 12 is provided to add stability to a central specimen support 14. Support 14 extends vertically upwardly from base 12 in the manner of pedestal. The support 14 includes a cylindrical sidewall 16 and a top or upper surface 18. A contoured form such as a shaped recess 20 is cast and/or precision machined along the top surface 18 to receive a dissection specimen such as the rodent brain specimen 21 shown in section in FIG. 2.

Figure 2:
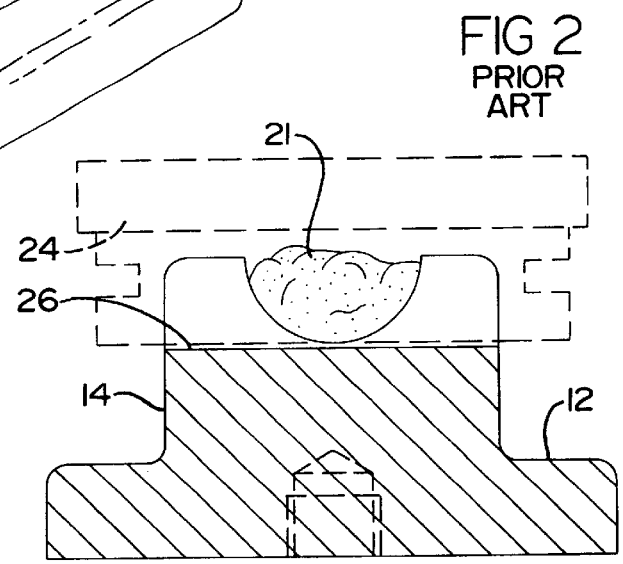
FIG. 2 is a view in section taken through a guide slot of FIG. 1 along section line 2—2 thereof.

A series of parallel slots 22 is formed in top surface 18 for guiding a dissection instrument such as razor 24, as shown in FIG. 2, through a dissection specimen such as the rodent brain 21. The slots 22 define a series of upstanding vertical support members in the form of parallel planar support plates 25. As the razor 24 slices through the rodent brain 21, bits of tissue and debris from the rodent brain are transferred, deposited and compacted on and along the floor 26 of each respective guide slot 22.

Because the guide slots are typically quite narrow, i.e., 0.011 inch wide, it is typically difficult to properly and thoroughly clean the specimen debris lodged within the guide slots 22. It is particularly difficult to remove the tissue and debris lodged within the lower or bottom portion of each guide slot along and on the guide slot floors 26.

Figure 3:
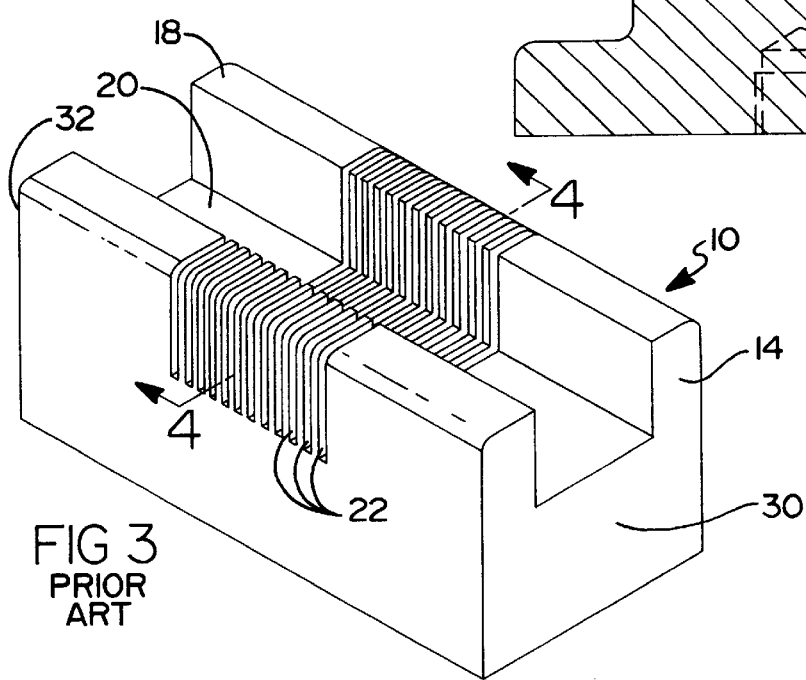
FIG. 3 is a view of another dissection specimen holder according to the prior art.

Another holder 10, constructed according to a conventional designs is shown in FIGS. 3 and 4. In this design, the base 12 is omitted and pedestal support 14 is in the shape of a grooved regular block. The recess 20 is formed as a rectangular groove or channel which opens out through opposed end walls 30, 32.

This design is also prone to the build-up and accumulation of tissue and other debris along the floor 26 of each groove 22. As in the case of the holder of FIGS. 1 and 2, the floors 26 of the guide slots 22 of the holder 10 of FIGS. 3 and 4 are also hard to clean thoroughly.

In order to facilitate cleaning of the holder 10, particularly within guide slots 22 and especially along the guide slot floors 26, the improved holder of FIG. 5 has been developed in accordance with a first embodiment of the present invention. The general outward appearance of the holder 10 of FIG. 5 is similar to that of FIG. 1, although the optional base 12 has been eliminated. In FIG. 6, an optional base 12 is show in dashed lines.

As best seen in FIGS. 6, 7 and 8, a major feature of the present invention is the provision of a cavity or chamber 36 formed through the bottom surface 38 of support 14. Although support 14 is shown as a generally cylindrical member, it may be formed with any suitable shape such as a rectangular, polygonal, or irregular shaped bar, block or column.

Chamber 36 maybe cast and/or machined into the interior of support 14 and may have a cylindrical shape as shown. Of course, any shape such as a hemispherical or frustoconical shape may be used to form and define chamber 36, as long as most and preferably all of the slots 22 communicate freely and directly with chamber 36.

As further seen in FIGS. 6, 7 and 8, the inner cylindrical wall 40 of cavity or chamber 36 extends upwardly within the holder 10 from the bottom surface 38 adjacent the bottom portion of chamber 36 and into a central portion of the holder. The inner wall 40 ends at a top portion of the cavity or chamber 36, over which extends a slotted or serrated roof 42.

Each of the slots 22 formed in the upper surface 18 of support 14 extends downwardly into the holder 10 and through the sidewall 16. The top portion of each slot 22 initially receives a dissection tool and guides it downwardly to the bottom portion of each respective slot until the tool bottoms out against one or both of the spaced apart floor portions 44 located on opposing sides of the sidewall. Floor portions 44 are separated by chamber 36.

The slots 22 may be spaced apart on 1 millimeter center-to-center spacings. Each slot 22 may be about 0.011 inch wide so as to closely receive and guide a common razor which typically has a width of about 0.010 inch.

It should be noted that the bottom portion of each slot 22 extends into, over and along the top portion of chamber 36 so as to allow tissue and other debris to freely pass directly into chamber 36. It can be appreciated that slots 22 may be easily cleaned by flushing cleaning fluid upwardly through chamber 36 and out of top surface 18 and/or downwardly through top surface 18 and out of chamber 36 adjacent bottom surface 38.

By positioning each pair of floor portions 44 of each slot 22 below each adjacent roof portion 42 of chamber 36, the cutting edge of the razor or other dissection tool will freely enter the open top portion of chamber 36 and thereby deposit or otherwise release specimen tissue directly into chamber 36. Moreover, because each floor portion 44 is located below the lowest or innermost support surface 46 of shaped and contoured recess 20, the razor is ensured of passing cleanly and completely through each section of specimen.

As seen in FIGS. 7 and 8, each plate 25 spans or bridges over and across the top portion of cavity 36. Preferably, only a relatively thin central section 48 of plate material separates the innermost support surface 46 of recess 20 from the roof 42 of chamber 36. This small surface area of each plate 25 reduces the chance of tissue and other specimen debris adhering to the walls of the plates 25 directly below and adjacent to recess 20.

Another embodiment of the invention is shown in FIGS. 9 and 10 wherein the holder of FIGS. 3 and 4 has been modified in accordance with the invention The general outward shape of the holder 10 of FIGS. 9 and 10 is substantially the same as that of FIGS. 3 and 4, except for the provision of an internal chamber or cavity 36.

Although recess 20 is in the shape of a rectangular groove or channel, and the chamber 36 is a substantially rectangular void underlying recess 20, all the structural relationships discussed above in connection with FIGS. 5 through 8 apply equally to FIGS. 9 and 10.

There has been disclosed heretofore the best embodiment of the invention presently contemplate. However, it is to be understood that the various changes and modifications may be made thereto without departing from the spirit of the invention.

What is claimed is:

1. A dissection apparatus, comprising:
   a support having a bottom surface portion, an upper surface portion and a sidewall interconnecting said upper and bottom surface portions;
   a contoured form provided on said upper surface portion for holding a sample for dissection;
   a plurality of slots formed in said upper surface portion extending across and communicating with said contoured form so as to define a plurality of tool guides; and
   a cavity formed in said support and communicating with said plurality of slots for receiving debris from said sample, said slots extending across and into said cavity.

2. The apparatus of claim 1, wherein said cavity extends from said bottom surface portion upwardly into a central portion of said support.

3. The apparatus of claim 1, wherein said cavity has a top portion and a bottom portion, wherein each of said plurality of slots has a top portion and a bottom portion, and wherein said bottom portion of each slot extends into and along said top portion of said cavity.

4. The apparatus of claim 1, wherein each one of said plurality of slots has a floor formed in said sidewall and wherein said cavity has a roof portion formed in said support.

5. The apparatus of 4, wherein each said floor portion of said slots is located below said roof portion of said cavity.

6. A dissection apparatus, comprising:
   a support having a support surface for supporting a specimen for dissection;
   a debris chamber formed in said support for receiving dissection debris;
   a plurality of spaced-apart support plates provided on said support defining said support surface and extending over the debris chamber;
   a plurality of dissection tool guide slots extending between said support plates;
   a pair of spaced-apart slotted floor portions located on opposite sides of said debris chamber, said floor portions defined between said support plates by said plurality of guide slots; and
   a roof extening under said support surface and over said chamber and defined by said plurality of plates.

7. The apparatus of claim 6, wherein said roof is positioned above said slotted floor portions.

* * * * *